US011129644B2

(12) United States Patent
Begg

(10) Patent No.: US 11,129,644 B2
(45) Date of Patent: Sep. 28, 2021

(54) SURGICAL DEVICE, SYSTEM, AND METHOD FACILITATING MINIMALLY-INVASIVE ACCESS TO AN INTERNAL SURGICAL SITE

(71) Applicant: COVIDIEN LP, Mansfield, MA (US)

(72) Inventor: Nikolai D. Begg, Wayland, MA (US)

(73) Assignee: Covidien LP, Mansfield, MA (US)

( * ) Notice: Subject to any disclaimer, the term of this patent is extended or adjusted under 35 U.S.C. 154(b) by 241 days.

(21) Appl. No.: 15/942,744

(22) Filed: Apr. 2, 2018

(65) Prior Publication Data

US 2018/0344351 A1    Dec. 6, 2018

Related U.S. Application Data

(60) Provisional application No. 62/515,579, filed on Jun. 6, 2017.

(51) Int. Cl.
| | | |
|---|---|---|
| A61B 17/34 | (2006.01) | |
| A61B 17/02 | (2006.01) | |
| A61B 17/00 | (2006.01) | |
| A61B 90/00 | (2016.01) | |

(52) U.S. Cl.
CPC ...... *A61B 17/3423* (2013.01); *A61B 17/0218* (2013.01); *A61B 17/3417* (2013.01); *A61B 17/3421* (2013.01); *A61B 17/0281* (2013.01); *A61B 2017/00349* (2013.01); *A61B 2017/3454* (2013.01); *A61B 2017/3488* (2013.01); *A61B 2017/3492* (2013.01); *A61B 2090/08021* (2016.02)

(58) Field of Classification Search
CPC .................. A61B 17/3423; A61B 17/0218
See application file for complete search history.

(56) References Cited

U.S. PATENT DOCUMENTS

| | | | | |
|---|---|---|---|---|
| 5,443,484 | A | * | 8/1995 | Kirsch ............... A61B 17/0281 604/164.04 |
| 5,653,718 | A | | 8/1997 | Yoon |
| 5,769,820 | A | | 6/1998 | Rammler |
| 8,771,223 | B2 | | 7/2014 | Patton et al. |
| 2008/0275306 | A1 | * | 11/2008 | Rebuffat .................. A61B 1/31 600/184 |

* cited by examiner

*Primary Examiner* — Si Ming Ku
(74) *Attorney, Agent, or Firm* — Carter, DeLuca & Farrell LLP

(57) ABSTRACT

A surgical device includes a tubular body, a proximal hub, and a plurality of tissue-engaging members. The tubular body includes a distally-facing surface. The proximal hub is disposed at a proximal end portion of the tubular body. The tubular body and the proximal hub cooperate to define a lumen extending therethrough. The plurality of tissue-engaging members extends distally from the distally-facing surface of the tubular body, is arranged annularly about the lumen, and is configured to engage tissue. A system includes the surgical device and a cannula and trocar assembly configured for insertion therethrough. Methods of use are also provided.

10 Claims, 4 Drawing Sheets

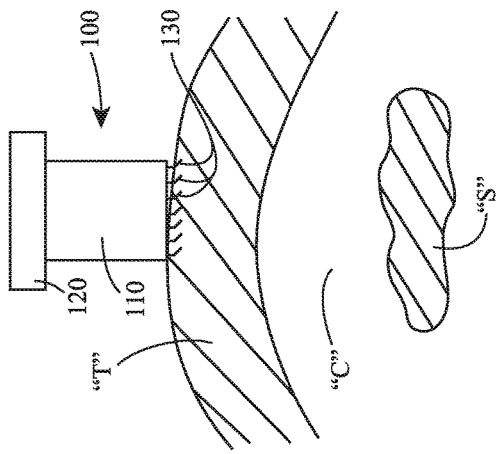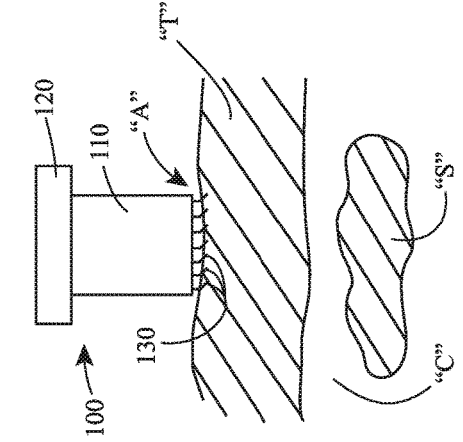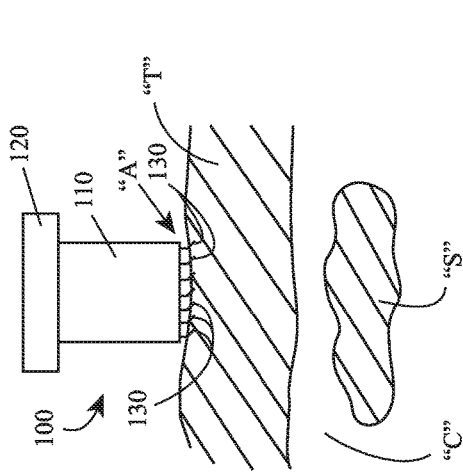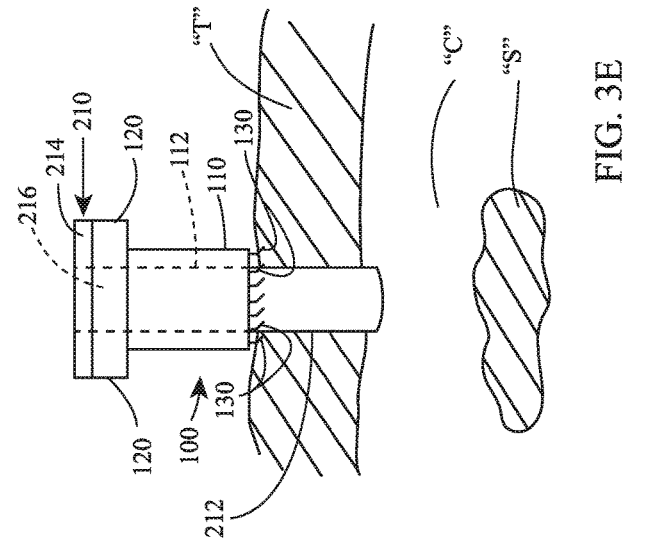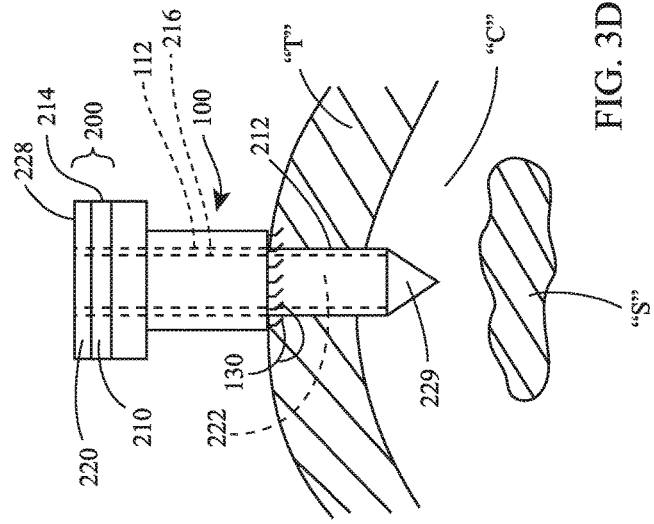

SURGICAL DEVICE, SYSTEM, AND METHOD FACILITATING MINIMALLY-INVASIVE ACCESS TO AN INTERNAL SURGICAL SITE

CROSS REFERENCE TO RELATED APPLICATION

The present application claims the benefit of and priority to U.S. Provisional Application Ser. No. 62/515,579, filed on Jun. 6, 2017 the entire contents of which are incorporated herein by reference.

BACKGROUND

Technical Field

The present disclosure relates to minimally-invasive surgical procedures and, more particularly, to a surgical device, system, and method facilitating minimally-invasive access to an internal surgical site for performing a surgical procedure therein.

Background of Related Art

In minimally-invasive surgical procedures, operations are carried out within an internal surgical site through small entrance openings. The entrance openings may be natural passageways or may be surgically created.

With respect to surgically created openings, for example, a trocar may be utilized to puncture tissue to provide access to the internal surgical site by way of a cannula extending through the tissue. The cannula, after removal of the trocar therefrom, allows for introduction of surgical instrumentation into the internal surgical site to carry out one or more surgical tasks within the internal surgical site.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a surgical device including a tubular body defining a longitudinal axis, a proximal end portion, and a distal end portion. The tubular body includes a distally-facing surface at the distal end portion thereof. The surgical device further includes a proximal hub disposed at the proximal end portion of the tubular body. The tubular body and the proximal hub cooperate to define a lumen extending therethrough. The surgical device further includes a plurality of tissue-engaging members extending distally from the distally-facing surface of the tubular body. The plurality of tissue-engaging members is arranged annularly about the lumen and configured to engage tissue.

In an aspect of the present disclosure, the plurality of tissue-engaging members is equally-spaced annularly about the lumen.

In another aspect of the present disclosure, each tissue-engaging member includes an angled portion. The angled portions of the tissue-engaging members are angled in a circumferential direction.

In still another aspect of the present disclosure, each tissue-engaging member includes a tissue-penetrating tip.

In yet another aspect of the present disclosure, the proximal hub defines a diameter greater than a diameter of the tubular body.

In still yet another aspect of the present disclosure, the plurality of tissue-engaging members is configured to engage tissue upon rotation of the tubular body about the longitudinal axis.

A surgical system provided in accordance with aspects of the present disclosure includes a surgical device defining a lumen extending longitudinally therethrough and a distally-facing surface. The surgical device further includes a plurality of tissue-engaging members extending distally from the distally-facing surface thereof. The system also includes a trocar configured for insertion through the lumen of the surgical device such that a distal tip of the trocar extends distally from the lumen of the surgical device.

In an aspect of the present disclosure, the system further includes a cannula. In such aspects, the trocar is configured for receipt within the cannula and the trocar and cannula are together configured for insertion through the lumen of the surgical device.

In another aspect of the present disclosure, a proximal hub of the cannula is configured to interfere with a proximal hub of the surgical device to inhibit further insertion of the cannula and trocar through the lumen of the surgical device.

In yet another aspect of the present disclosure, the plurality of tissue-engaging members is equally-spaced annularly about the lumen.

In still another aspect of the present disclosure, each tissue-engaging member includes an angled portion angled in a circumferential direction.

In still yet another aspect of the present disclosure, each tissue-engaging member includes a tissue-penetrating tip.

In another aspect of the present disclosure, the plurality of tissue-engaging members is configured to engage tissue upon rotation of the surgical device about a longitudinal axis thereof.

A method provided in accordance with aspects of the present disclosure includes engaging a surgical device on a surface of tissue, inserting a cannula and trocar assembly including a trocar disposed within a cannula through the surgical device to penetrate tissue and extend into an internal surgical site, and withdrawing the trocar from within the cannula.

In an aspect of the present disclosure, engaging the surgical device on the surface of tissue includes rotating the surgical device about a longitudinal axis thereof to engage the surgical device with the surface of tissue.

In another aspect of the present disclosure, with the surgical device engaged on the surface of tissue, the method further includes elevating the tissue by pulling the surgical device proximally.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements and:

FIGS. 3A-3E are schematic views illustrating use of the surgical device of FIG. 1 together with the cannula and trocar assembly of FIG. 2A in accordance with the present disclosure to provide minimally-invasive access to an internal surgical site for performing a surgical procedure therein.

DETAILED DESCRIPTION

The present disclosure provides a surgical device, system, and method facilitating minimally-invasive access to an internal surgical site for performing a surgical procedure therein.

Figure 1:
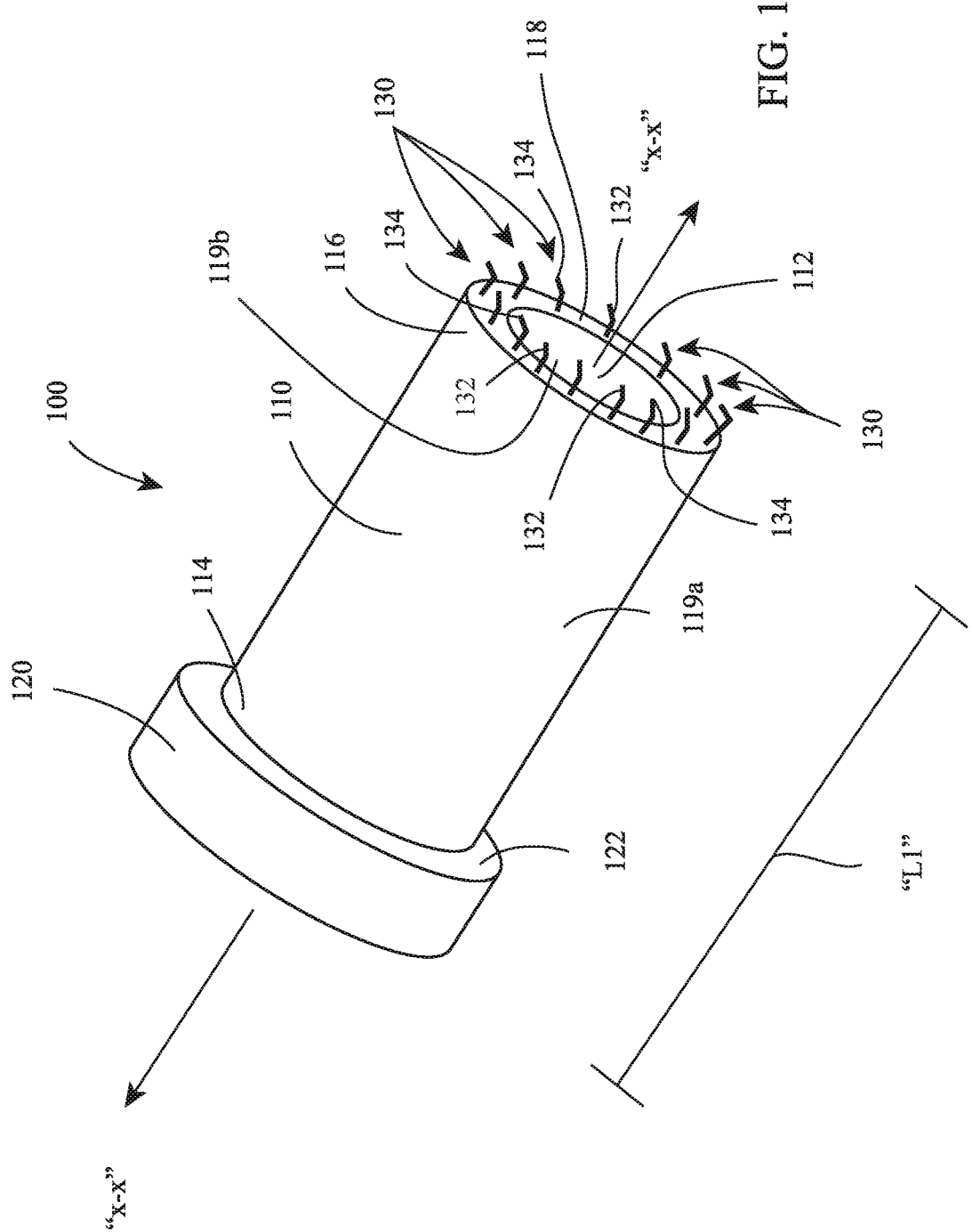
FIG. 1 is a perspective view of a surgical device provided in accordance with the present disclosure configured to facilitate minimally-invasive access to an internal surgical site for performing a surgical procedure therein.

Turning to FIG. 1, a surgical device provided in accordance with the present disclosure and configured to facilitate minimally-invasive access to an internal surgical site for performing a surgical procedure therein is shown generally designated by reference numeral 100. Surgical device 100 generally includes a tubular body 110, a proximal hub 120, and a plurality of tissue-engaging members 130.

Tubular body 110 has a generally cylindrical configuration, defines a longitudinal axis "X-X," and, together with proximal hub 120, includes a lumen 112 extending longitudinally therethrough. Lumen 112 defines a sufficient diameter to enable insertion of a cannula and trocar assembly 200 (FIGS. 2A-2B) therethrough. Tubular body 110 further defines a proximal end portion 114 and a distal end portion 116. A distally-facing surface 118 of tubular body 110 is defined at distal end portion 116 thereof. Distally-facing surface 118 defines a ring-shaped configuration and is disposed annularly about lumen 112. Distally-facing surface 118 extends in generally transverse orientation relative to outer and inner cylindrical surfaces 119a, 119b, respectively, of tubular body 110.

Proximal hub 120 is disposed at proximal end portion 114 of tubular body 110 and may be monolithically formed therewith or otherwise fixedly engaged thereto. Proximal hub 120 defines a greater diameter than tubular body 110 to form an annular lip 122 extending radially outwardly from tubular body 110. Annular lip 122 of proximal hub 120 facilitates grasping and manipulating surgical device 100. Tubular body 110 and proximal hub 120 cooperate to define an operative length "L1" of surgical device 100.

Tissue-engaging members 130 extend distally from distally-facing surface 118 of tubular body 110 and are disposed annularly about lumen 112 of tubular body 110. Tissue-engaging members 130 are equally-spaced annularly about distally-facing surface 118, although other configurations are also contemplated. Further, greater of fewer tissue-engaging members 130 from those illustrated may be provided. Tissue-engaging members 130 may take the form of tines, barbs, teeth, etc.

Each tissue-engaging member 130 defines an angled portion 132 culminating in a tissue-penetrating tip 134. Angled portions 132 of tissue-engaging members 130 are angled similarly relative to each other and are angled in a circumferential direction. As a result of this configuration of tissue-engagement members 130, surgical device 100 may be rotated about longitudinal axis "X-X" (in the direction angled portions 132 of tissue-engaging members 130 are angled) to drive tissue-penetrating tips 134 of tissue-engaging members 130 into engagement with tissue. By engaging tissue in this manner, tissue-engaging members 130 are not disengaged from tissue upon proximal pulling of surgical device 100 relative to tissue, thus enabling surgical device 100 to be pulled proximally to elevate tissue engaged therewith. Other suitable configurations of tissue-engaging members 130 that enable engagement of surgical device 100 with tissue and inhibit disengagement upon proximal pulling of surgical device 100 are also contemplated. It is noted that tissue-engaging members 130 may be configured only to penetrate tissue to a depth necessary to sufficiently engage tissue so as to enable elevation thereof upon proximal pulling of surgical device 100. That is, tissue-engaging members 130 need not fully penetrate tissue into an internal surgical site.

Figure 2A:
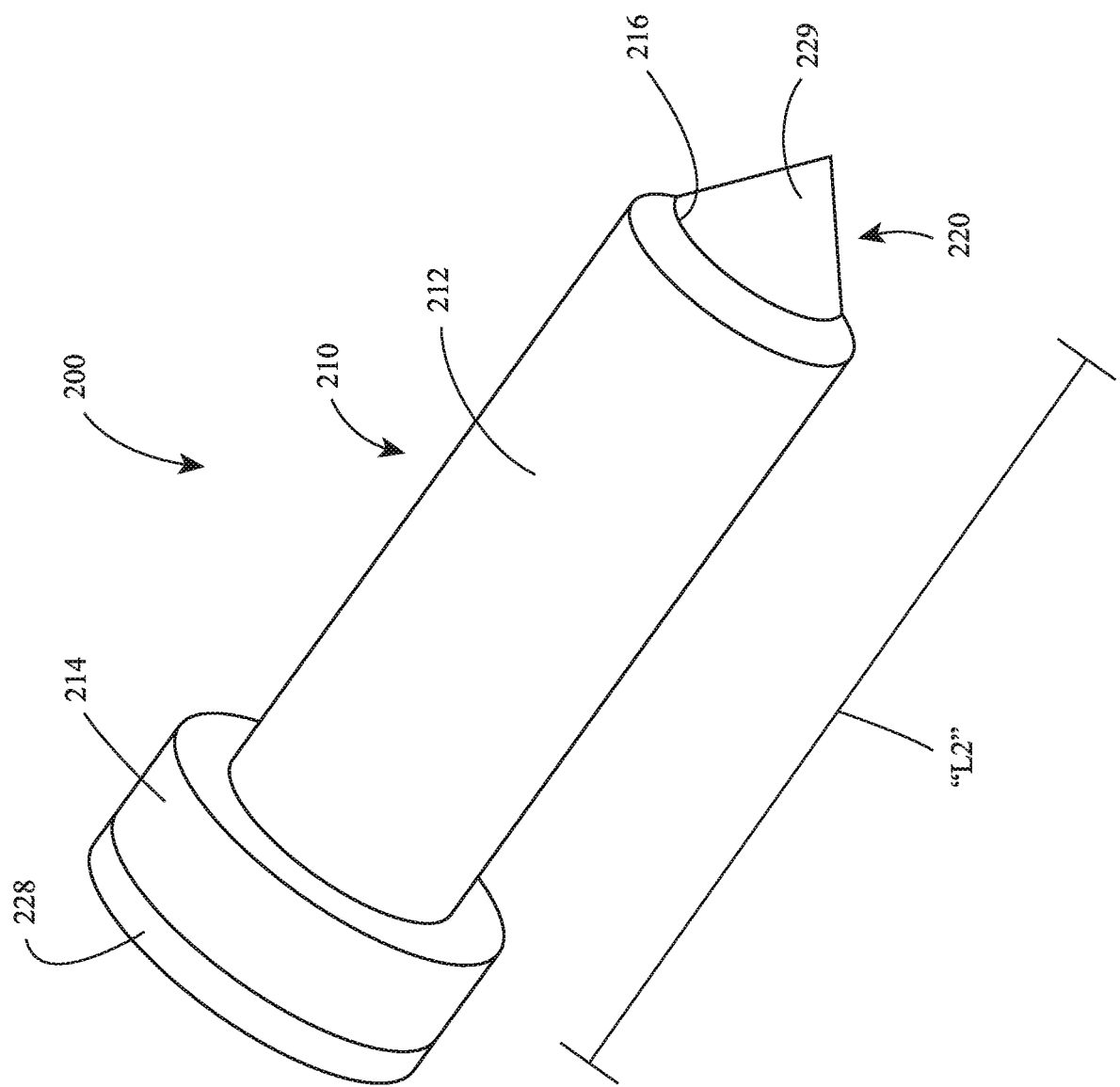
FIG. 2A is a perspective view of a cannula and trocar assembly provided in accordance with the present disclosure, disposed in an assembled condition.
Figure 2B:
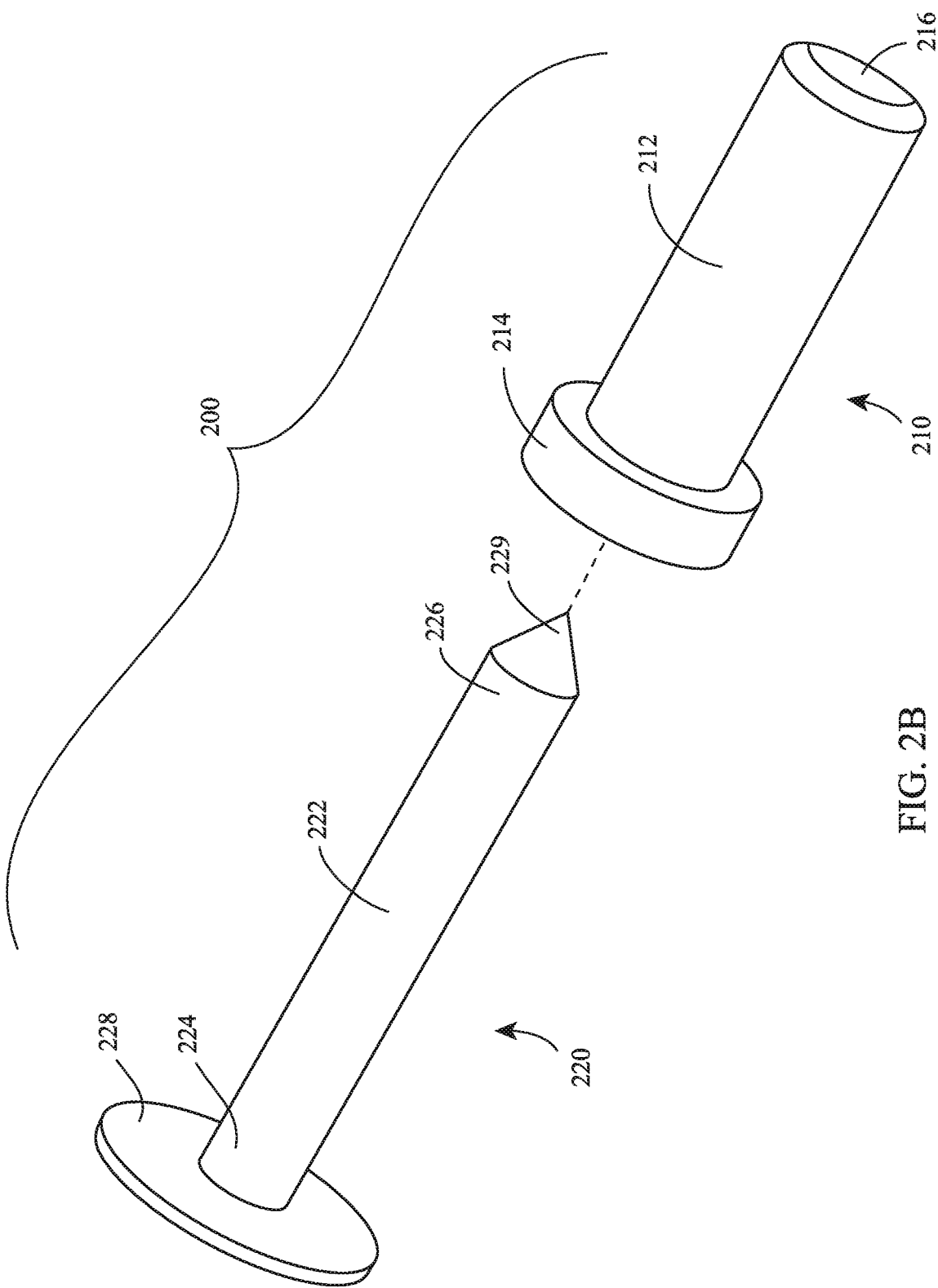
FIG. 2B is a perspective view of the cannula and trocar assembly of FIG. 2A, disposed in a disassembled condition.

Turning to FIGS. 2A-2B, a cannula and trocar assembly provided in accordance with the present disclosure is shown generally designated by reference numeral 200. Cannula and trocar assembly 200 includes a cannula 210 and a trocar 220.

Cannula 210 of cannula and trocar assembly 200 includes a tubular body 212 and a proximal hub 214 disposed at a proximal end portion of tubular body 212. Tubular body 212 and proximal hub 214 cooperate to define a lumen 216 extending longitudinally therethrough. Tubular body 212 defines a diameter sufficiently small so as to permit insertion of tubular body 212 through lumen 112 of surgical device 100. Proximal hub 214, on the other hand, defines a diameter greater than the diameter of lumen 112 of surgical device 100 such that a depth of insertion of tubular body 212 through lumen 112 of surgical device 100 is limited by interference between proximal hub 214 of cannula 210 and proximal hub 120 of surgical device 100.

Trocar 220 of cannula and trocar assembly 200 includes a shaft 222 defining a proximal end portion 224 and a distal end portion 226 and a proximal hub 228 disposed at proximal end portion 224 of shaft 222. Trocar 220 further includes a conical tissue-penetrating distal tip 229 disposed at distal end portion 226 of shaft 222, although other suitable features, e.g., a cutting blade (not shown), configured to facilitate penetration of tissue and advancement of trocar 220 therethrough are alternatively or additionally contemplated. Shaft 222 of trocar 220 defines a diameter sufficiently small to permit insertion of shaft 222 through lumen 216 of cannula 210 and a length sufficiently great such that, with trocar 220 fully inserted into cannula 210 (see FIG. 2A) such that proximal hub 228 of trocar 220 abuts proximal hub 214 of cannula 210, at least a portion of distal tip 229 extends distally from cannula 210. Cannula 210 and/or trocar 220 may include releasable locking features (not shown) configured to enable releasable locking of trocar 220 with cannula 210 in the fully inserted position (FIG. 2A).

Referring to FIGS. 1-2B, with trocar 220 in the fully inserted position relative to cannula 210 (see FIG. 2A), tubular body 212 of cannula 210 and the portion of distal tip 229 of trocar 220 that extends distally from tubular body 210 cooperate to define an operative length "L2" that is greater than the operative length "L1" of surgical device 100. The difference between the operative length "L2" of cannula and trocar assembly 200 and the operative length "L1" of surgical device 100 defines the extent to which cannula and trocar assembly 200 extends distally from surgical device 100 when cannula and trocar assembly 200 is fully inserted into lumen 112 of surgical device 100, e.g., the position wherein proximal hub 214 of cannula 210 abuts proximal hub 120 of surgical device 100. Surgical device 100 and/or cannula and trocar assembly 200 may be configured relative to one another to achieve a desired extent that cannula and trocar assembly 200 extends distally from surgical device 100 when cannula and trocar assembly 200 is fully inserted into lumen 112 of surgical device 100. In embodiments, a plurality of surgical devices 100 having different operative lengths "L1" and/or lumen diameters may be provided, e.g., as part of a kit, for use with various different cannula and trocar assemblies 200.

Turning now to FIGS. 3A-3E the use of surgical device 100 in conjunction with cannula and trocar assembly 200 for providing minimally-invasive access to an internal surgical site is detailed.

Initially, with reference to FIG. 3A, surgical device 100 is positioned at a surgical access location "A" on a surface of tissue "T" such that tissue-engaging members 130 of surgical device 100 are positioned adjacent to or in contact with the surface of tissue "T."

With reference to FIG. 3B, once the above-noted position of surgical device 100 has been achieved, surgical device 100 is rotated about longitudinal axis "X-X" thereof to drive tissue-penetrating tips 134 (FIG. 1) of tissue-engaging members 130 into engagement with tissue "T," thereby engaging surgical device 100 with tissue "T" at the surgical access location "A."

Referring to FIG. 3C, with surgical device 100 engaging tissue "T" at the surgical access location "A," proximal hub 120 of surgical device 100 may be grasped and pulled proximally to elevate tissue "T" thereby enlarging the internal surgical site, e.g., internal body cavity "C." In this manner, tissue "T" is spaced-apart from internal structures "S" within the internal body cavity "C."

Turning to FIG. 3D, with surgical device 100 retaining tissue "T" in an elevated condition such that tissue "T" is spaced-apart from internal structures "S" within the internal body cavity "C," cannula and trocar assembly 200, in the fully assembled condition thereof (see FIG. 2A), is inserted, lead by distal tip 229, through lumen 112 of surgical device 100 to pierce and penetrate through tissue "T." Cannula and trocar assembly 200, more specifically, is advanced through tissue "T" until distal tip 229 of trocar 220 and at least the distal end portion of tubular body 212 of cannula 210 are disposed within the internal body cavity "C." As noted above, the extent to which cannula and trocar assembly 200 is capable of extending distally from surgical device 100 is determined by the difference between the operative length "L2" of cannula and trocar assembly 200 and the operative length "L1" of surgical device 100 (see FIGS. 1 and 2A). Thus, the extent to which cannula and trocar assembly 200 extends into the internal body cavity "C" is determined by the above-noted difference and the thickness of tissue "T." Accordingly, by selecting an appropriate surgical device 100 relative to the cannula and trocar assembly 200, and/or by utilizing surgical device 100 to elevate tissue "T," as noted above, cannula and trocar assembly 200 can be inhibited from being advanced too far into internal body cavity "C" and, thus, damage to internal structures "S" can be inhibited.

With reference to FIG. 3E, once distal tip 229 of trocar 220 of cannula and trocar assembly 200 has been utilized to penetrate tissue "T" and create an access opening therethrough and into the internal body cavity "C," surgical device 100 may be released or returned distally to allow the elevated tissue "T" to return to its initial position. Trocar 220 may also be removed from cannula and trocar assembly 200, leaving cannula 210 disposed within surgical device 100. With lumen 212 of cannula 210 now vacant, surgical instrumentation (not shown) may be inserted therethrough to perform a surgical procedure within the internal body cavity "C."

Once the surgical procedure is complete, cannula 210 may be withdrawn proximally from surgical device 100. Thereafter, surgical device 100 may be rotated about longitudinal axis "X-X" in the opposite direction as surgical device 100 was rotated to engage surgical device 100 with tissue "T," to thereby disengage surgical device 100 from tissue "T."

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical device, comprising:
    a tubular body defining a longitudinal axis, a proximal end portion, and a distal end portion, the tubular body including a distally-facing surface at the distal end portion thereof;
    a proximal hub disposed at the proximal end portion of the tubular body, the tubular body and the proximal hub cooperating to define a lumen extending therethrough; and
    a plurality of tissue-engaging members extending distally from the distally-facing surface of the tubular body, the plurality of tissue-engaging members arranged annularly about the lumen and configured to engage tissue, each of the tissue engaging members including a longitudinally-extending portion extending distally from the distally-facing surface in a longitudinal direction and an angled portion extending from the longitudinally-extending portion in a circumferential direction at an obtuse angle relative to the longitudinally-extending portion,
    wherein the angled portion of each tissue-engaging member includes a fixed proximal end attached to the longitudinally-extending portion and a free distal end, the free distal end of each of the tissue-engaging members oriented towards an adjacent tissue-engaging member such that the free distal ends of the angled portions of the tissue-engagement members are collectively oriented in a clockwise or counterclockwise direction about a circle intersecting the free distal ends.

2. The surgical device according to claim 1, wherein the plurality of tissue-engaging members is equally-spaced annularly about the lumen.

3. The surgical device according to claim 1, wherein each of the tissue-engaging members includes a tissue-penetrating tip disposed at the free distal end of the angled portion.

4. The surgical device according to claim 1, wherein the proximal hub defines a diameter greater than a diameter of the tubular body.

5. The surgical device according to claim 1, wherein the plurality of tissue-engaging members is configured to engage tissue upon rotation of the tubular body about the longitudinal axis.

6. A surgical device, comprising:
    a tubular body defining a longitudinal axis, a proximal end portion, and a distal end portion, the tubular body including a distally-facing surface at the distal end portion thereof;

a proximal hub disposed at the proximal end portion of the tubular body, the tubular body and the proximal hub cooperating to define a lumen extending therethrough; and a plurality of tissue-engaging members extending distally from the distally-facing surface of the tubular body, the plurality of tissue-engaging members arranged to define a cylinder disposed about the lumen, each of the tissue-engaging members including a longitudinal portion and an angled portion extending from the longitudinal portion at an obtuse angle relative to the longitudinal portion, wherein the angled portion of each tissue-engaging member is angled circumferentially relative to the longitudinal portion such that the tissue-engagement members do not extend radially inwardly or outwardly from the cylinder.

7. The surgical device according to claim 6, wherein the plurality of tissue-engaging members is equally-spaced annularly about the lumen.

8. The surgical device according to claim 6, wherein each of the tissue-engaging members includes a tissue-penetrating tip disposed at a free end of the angled portion.

9. The surgical device according to claim 6, wherein the proximal hub defines a diameter greater than a diameter of the tubular body.

10. The surgical device according to claim 6, wherein the plurality of tissue-engaging members is configured to engage tissue upon rotation of the tubular body about the longitudinal axis.

* * * * *